(12) United States Patent
Uragg et al.

(10) Patent No.: US 7,507,816 B2
(45) Date of Patent: Mar. 24, 2009

(54) PHARMACEUTICAL PREPARATIONS COMPRISING SUBSTITUTED BETA-AMINOALCOHOLS

(75) Inventors: Heinz Uragg, Stolberg (DE); Corinna Maul, Aachen (DE); Helmut Buschmann, Esplugues de Llobregat (DE); Bernd Sundermann, Aachen (DE); Hagen-Heinrich Hennies, Simmerath (DE)

(73) Assignee: Gruenenthal GmbH, Aachen (DE)

( * ) Notice: Subject to any disclaimer, the term of this patent is extended or adjusted under 35 U.S.C. 154(b) by 557 days.

(21) Appl. No.: 10/866,099

(22) Filed: Jun. 14, 2004

(65) Prior Publication Data

US 2005/0020691 A1 Jan. 27, 2005

Related U.S. Application Data

(63) Continuation of application No. PCT/EP02/13910, filed on Dec. 9, 2002.

(30) Foreign Application Priority Data

Dec. 14, 2001 (DE) ................................ 101 64 581

(51) Int. Cl.
| | |
|---|---|
| C07D 267/02 | (2006.01) |
| C07D 267/04 | (2006.01) |
| C07D 267/06 | (2006.01) |
| C07D 267/08 | (2006.01) |
| C07D 267/10 | (2006.01) |
| C07D 281/02 | (2006.01) |
| C07D 281/04 | (2006.01) |
| C07D 281/06 | (2006.01) |

(52) U.S. Cl. .................. 540/544; 540/660; 514/211.02; 514/212.02

(58) Field of Classification Search .............. 514/231.2, 514/231.5
See application file for complete search history.

(56) References Cited

U.S. PATENT DOCUMENTS 3,652,589 A * 3/1972 Flick .......................... 548/578

FOREIGN PATENT DOCUMENTS

| DE | 1146068 | | 3/1963 |
|---|---|---|---|
| DE | 19547766 | | 6/1977 |
| JP | 01131170 | | 5/1989 |
| SU | 546607 | * | 2/1977 |

OTHER PUBLICATIONS

Takahashi T et. al. Yakugaku Zasshi, 1959, 79, 1087-1091, STN Abstract.*

Martin Ch. Frink et al., "Influence of Tramadol on Neurotransmitter Systems of the Rat Brain", Arzneim-Forsch./Drug Research, 1996, pp. 1029-1036, vol. 46(II).
Torizo Takahashi et al., "Syntheses of Analgesics- (XXIII) Animocyclopentane Derivs.", Chemical Abstract.
K.B. Erzhanov et al., "Synthesis of 1-Hydroxy- and 1-Amino-2-(Dialkylaminomethyl) Cyclohexanecarbo Nitriles", 2002, Chemical Abstract.
Olga Caamano et al., "Semi-rigid Models of Butyrophenones: Trans-phenyl-[2-(1-Piperidinylmethyl) Cyclopentyl) Methanone", 2002, Chemical Abstract.
Zh. A. Abenov et al., "Synthesis of Some Derivatives of 2-Aminomethylcyclohexanones", 2002, Chemical Abstract.
E. Ravini et al., "Derivatives of 4,4-Disubstituted Cyclohexane. VI. Tertiary Aminomethylcyclohexanols as Antispasmodics", 1974, Chemical Abstract.
Olga Caamano et al., "Synthesis of Semi-rigid Models of Butyrophenone Neuroleptic Drugs. I. Evaluation of a Route Leading to Phenyl Trans-2-(1-Piperidinylmethyl) Cyclohexyl Ketone", 2002, Chemical Abstract.
"1-Isopropyl-2-Piperidinomethyl-Cyclohexanol", 2000, pp. 1-5, Chemical Abstract, XP-002232916.
"1-(Hexahydroazepinyl-(1))-2-Methyl-3-Phenyl-Pentanol-(3)", 2000, pp. 1-2, Chemical Abstract, XP-002232917.
Chemical Abstract, Jan. 21, 1974, p. 404, vol. 80, No. 3, Columbus, Ohio, USA, XP-002232907.
Chemical Abstract, Mar. 2, 1998, p. 572, vol. 128, No. 9, Columbus, Ohio, USA, XP-002232908.
Chemical Abstract, Feb. 29, 1988, p. 660, vol. 108, No. 9, Columbus, Ohio, USA, XP-002232909.
Chemical Abstract, Apr. 13, 1987, p. 621, vol. 106, No. 15, Columbus, Ohio, USA, XP-002232910.
Chemical Abstract, Sep. 11, 1972, p. 459, vol. 77, No. 11, Columbus, Ohio, USA, XP-002232911.
Chemical Abstract, Sep. 14, 1970, p. 297, vol. 73, No. 11, Columbus, Ohio, USA, XP-002232912.
Chemical Abstract, Dec. 4, 1967, p. 10225, vol. 67, No. 23, Columbus, Ohio, USA, XP-002232913.
Chemical Abstract, Feb. 27, 1967, p. 3589, vol. 66, No. 9, Columbus, Ohio, USA, XP-002232914.
Chemical Abstract, Mar. 2, 1964, p. 5356F, vol. 60, No. 5, Columbus, Ohio, USA, XP-002232915.

* cited by examiner

*Primary Examiner*—Shaojia Anna Jiang
*Assistant Examiner*—Eric S Olson
(74) *Attorney, Agent, or Firm*—Crowell & Moring LLP

(57) ABSTRACT

Pharmaceutical compositions containing substituted aminoalcohols, the use of preparations containing substituted aminoalcohols for treatment of conditions such as pain, emesis, neurotropic conditions, cardiovascular diseases, urinary incontinence, diarrhea, pruritus, alcohol or drug dependency, inflammation, depression, decreased vigilance, or depressed libido, as well as 2-(aminomethyl)cycloalkane-1-ol compounds and a process for their preparation.

20 Claims, No Drawings

PHARMACEUTICAL PREPARATIONS COMPRISING SUBSTITUTED BETA-AMINOALCOHOLS

CROSS REFERENCE TO RELATED APPLICATIONS

This application is a continuation of international patent application no. PCT/EP02/13910, filed Dec. 9, 2002 designating the United States of America and published in German as WO 03/051353, the entire disclosure of which is hereby incorporated herein by reference. Priority is claimed based on Federal Republic of Germany patent application no. DE 101 64 581.3, filed Dec. 14, 2001.

BACKGROUND OF THE INVENTION

The present invention relates to pharmaceutical preparations containing substituted aminoalcohols and to the use of substituted aminoalcohols for the production of pharmaceutical preparations and to substituted 2-(aminomethyl)cycloalkan-1-ol compounds and processes for the production thereof.

The treatment of pain is of great medical significance. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is evident from the large number of scientific papers relating to applied analgesia and to basic nociception research which have appeared in recent times.

SUMMARY OF THE INVENTION

It is therefore the object of the invention to provide novel pharmaceutical preparations for the treatment of pain.

This and other objects have been achieved in accordance with the present invention by providing pharmaceutical preparations containing aminoalcohols of the formula I described hereinafter, since these pharmaceutical preparations, in particular, exhibit an excellent analgesic action and may be used for the treatment of pain, as an antiemetic and/or a nootropic (neurotropic), for the treatment of cardiovascular diseases, urinary incontinence, diarrhoea, pruritus, dependency on alcohol and/or drugs and/or medicines, and/or inflammation, for the treatment of depression, to increase vigilance and/or libido.

The invention therefore provides pharmaceutical preparations containing aminoalcohols corresponding to formula I

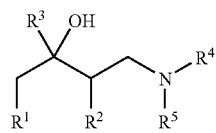

in which $R^1$ and $R^2$, are identical or different and each denote a linear or branched, saturated or unsaturated aliphatic residue, or together form a $(CH_2)_n$ chain, wherein n denotes an integer, $R^3$ denotes a linear or branched, saturated or unsaturated aliphatic residue, a saturated or unsaturated cycloaliphatic group, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system, $R^4$ and $R^5$ together form a $(CH_2)_m$ chain, wherein m denotes an integer and optionally one or more $CH_2$ groups may be replaced by oxygen, in the form of the diastereomers thereof, the enantiomers thereof and mixtures thereof—including the racemates thereof—and in the form of corresponding bases, salts and solvates as active ingredient with the exception of:
compounds corresponding to formula Ia,

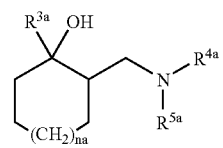

in which na denotes 0, 1 or 2, $R^{3a}$ denotes a phenyl residue, which is substituted in the meta position with an alkoxy group with 1-3 carbons or an aralkoxy group and $R^{4a}$ and $R^{5a}$ together form, including the nitrogen atom, one of the following rings:

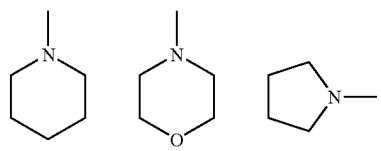

compounds corresponding to formula Ib,

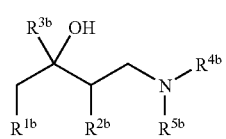

in which $R^{1b}$ denotes a lower alkyl residue or a phenyl residue, $R^{2b}$ denotes a lower alkyl residue, $R^{4b}$ and $R^{5b}$ together form a pyrrolidine or a piperidine ring and $R^{3b}$ denotes one of the following residues:

in which $R^I$ denotes hydrogen, a lower alkyl residue or a lower alkoxy residue, $R^{II}$ denotes hydrogen or a lower alkyl residue, $R^{III}$ denotes hydrogen, halogen, a trihalomethyl residue, a lower alkyl residue or a lower alkoxy residue and $R^{IV}$ denotes a lower alkoxy residue;

and

-1-benzyl-2-(piperidin-1-yl-methyl)-cyclohexan-1-ol, 1-phenyl-2-(piperidin-1-ylmethyl)-cyclohexan-1-ol, 3-(4-methylphenyl)-2-n-propyl-1-pyrrolidin-1-ylpentan-3-ol and 3-(phenyl)-2-n-propyl-1-pyrrolidin-1-ylpentan-3-ol;

and optionally physiologically acceptable auxiliary substances.

Pharmaceutical preparations are preferred which contain at least one compound corresponding to formula I, in which $R^1$ and $R^2$ are identical or different and each denote a linear or branched, saturated or unsaturated aliphatic $C_{1-6}$ residue, or together form a $(CH_2)_n$ chain, wherein n denotes an integer from 2-9, $R^3$ denotes a linear or branched, saturated or unsaturated aliphatic $C_{1-6}$ residue, a saturated or unsaturated cycloaliphatic $C_{3-7}$ residue, a phenyl residue or a five- or six-membered heteroaryl residue, wherein the respective ring system may optionally be mono- or polysubstituted and/or attached via a linear or branched, saturated or unsaturated aliphatic $C_{1-5}$ bridge, $R^4$ and $R^5$ together form a $(CH_2)_m$ chain, wherein m denotes an integer from 4-6 and optionally one or more $CH_2$ groups may be replaced by oxygen with the exception of the above-excepted compounds.

Pharmaceutical preparations are additionally preferred which contain at least one compound corresponding to formula I, in which:

$R^1$ and $R^2$, identical or different, in each case denote a linear or branched, saturated or unsaturated aliphatic $C_{1-3}$ residue, or together form a $(CH_2)_n$ chain, wherein n denotes an integer from 2-9, $R^3$ denotes a linear or branched, saturated or unsaturated aliphatic $C_{1-3}$ residue, a saturated or unsaturated cycloaliphatic $C_{5-6}$ residue, a phenyl residue or a five- or six-membered heteroaryl residue, wherein the respective ring system may optionally be mono- or polysubstituted with halogen, an alkyl group, an alkoxy group and/or a trihalogenated alkyl group and/or may be attached via a linear or branched, saturated or unsaturated aliphatic $C_{1-3}$ bridge, $R^4$ and $R^5$ together form a $(CH_2)_m$ chain, wherein m denotes an integer from 4-6 and optionally one or more $CH_2$ groups may be replaced by oxygen with the exception of the above-excepted compounds.

Pharmaceutical preparations are additionally preferred which contain at least one compound corresponding to formula I, in which $R^1$ and $R^2$ each denote a methyl group, or together form a $(CH_2)_n$ chain, wherein n is 2, 3, 4, 5 or 9, $R^3$ denotes a vinyl residue, a cyclopentyl residue, a cyclohexyl residue, a thiophenyl residue or a phenyl residue, wherein the cyclohexyl residue may optionally be attached via a methylene bridge or the phenyl residue may optionally be mono- or polysubstituted with fluorine, chlorine, a methyl group, an isopropyl group, a methoxy group and/or a trifluoromethyl group and/or may optionally be attached via a linear saturated aliphatic $C_{1-3}$ bridge or an ethynyl bridge, $R^4$ and $R^5$ together form a $(CH_2)_m$ chain, wherein m denotes 4, 5 or 6 with the exception of the above-excepted compounds.

Pharmaceutical preparations are particularly preferred which contain at least one compound corresponding to formula II,

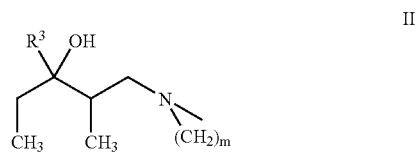

in which m denotes an integer from 4-6, $R^3$ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system with the exception of the above-excepted compounds.

Pharmaceutical preparations are particularly preferred which contain at least one compound corresponding to formula III,

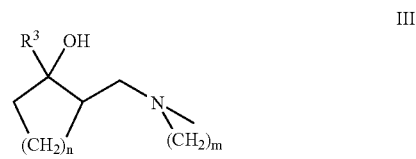

in which n denotes an integer from 2-9 and m denotes an integer from 4-6 and $R^3$ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system with the exception of the above-excepted compounds.

Pharmaceutical preparations are additionally preferred which contain at least one compound corresponding to formula II or III, in which $R^3$ denotes a linear or branched, saturated or unsaturated aliphatic $C_{1-6}$ residue, a saturated or unsaturated cycloaliphatic $C_{3-7}$ residue, a phenyl residue or a five- or six-membered heteroaryl residue, wherein the respective ring system may optionally be mono- or polysubstituted and/or attached via a linear or branched, saturated or unsaturated aliphatic $C_{1-5}$ bridge and the other symbols have the above-stated meanings, with the exception of the above-excepted compounds.

Pharmaceutical preparations are additionally preferred which contain at least one compound corresponding to formula II or III, in which R³ denotes a linear or branched, saturated or unsaturated aliphatic $C_{1-3}$ residue, a saturated or unsaturated cycloaliphatic $C_{5-6}$ residue, a phenyl residue or a five- or six-membered heteroaryl residue, wherein the respective ring system may optionally be mono- or polysubstituted with halogen, an alkyl group, an alkoxy group and/or a trihalogenated alkyl group and/or may be attached via a linear or branched, saturated or unsaturated aliphatic $C_{1-3}$ bridge and the other symbols have the above-stated meanings, with the exception of the above-excepted compounds.

Pharmaceutical preparations are additionally preferred which contain at least one compound corresponding to formula II or III, in which R³ denotes a vinyl residue, a cyclopentyl residue, a cyclohexyl residue, a thiophenyl residue or a phenyl residue, wherein the cyclohexyl residue may optionally be attached via a methylene bridge or the phenyl residue may optionally be mono- or polysubstituted with fluorine, chlorine, a methyl group, an isopropyl group, a methoxy group and/or a trifluoromethyl group and/or may optionally be attached via a linear saturated aliphatic $C_{1-3}$ bridge or an ethynyl bridge and the other symbols have the above-stated meanings, with the exception of the above-excepted compounds.

A "heteroaryl group" is understood to mean an optionally mono- or polysubstituted, five- to seven-membered aromatic residue with at least one, optionally 2, 3, 4 or 5 heteroatoms, which may be identical or different, which residue may be part of a polycyclic system. Preferred heteroatoms are nitrogen, oxygen and sulfur. Heteroaryl residues are particularly preferably selected from the group consisting of pyrrolyl, indolyl, furyl(furanyl), benzofuranyl, thienyl(thiophenyl), benzothienyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl and phenothiazinyl residues. Attachment may be effected via any desired bondable ring atom. The optionally present substituents may be identical or different and attached to any desired, bondable ring atom.

An "aryl residue" is understood to mean an optionally mono- or polysubstituted aromatic residue, which may be part of a polycyclic system. A phenyl residue is particularly preferred. Attachment may be effected via any desired bondable ring atom. The optionally present substituents may be identical or different and attached to any desired, bondable ring atom.

Very particularly preferred are pharmaceutical preparations containing at least one compound selected from the group consisting of:
1-(2,3-Dichloro-phenyl)-2-pyrrolidin-1-ylmethyl-cyclohexanol
2-Pyrrolidin-1-ylmethyl-1-p-tolyl-cyclohexanol
1-(4-Methoxy-phenyl)-2-pyrrolidin-1-ylmethyl-cyclohexanol
1-Phenyl-2-pyrrolidin-1-ylmethyl-cyclopentanol
1-(4-chloro-phenyl)-2-pyrrolidin-1-ylmethyl-cyclopentanol
1-Benzyl-2-pyrrolidin-1-ylmethyl-cyclopentanol
1-(4-Fluoro-3-methyl-phenyl)-2-pyrrolidin-1-ylmethyl-cyclopentanol
2-Pyrrolidin-1-ylmethyl-1-o-tolyl-cyclopentanol
2-Pyrrolidin-1-ylmethyl-1-vinyl-cyclopentanol
1-(4-tert-Butyl-phenyl)-2-pyrrolidin-1-ylmethyl-cyclopentanol
2-Pyrrolidin-1-ylmethyl-bicyclopentyl-1-ol
2-Pyrrolidin-1-ylmethyl-1-m-tolyl-cyclopentanol
1-Cyclohexyl-2-pyrrolidin-1-ylmethyl-cyclopentanol
1-(4-Fluoro-phenyl)-2-pyrrolidin-1-ylmethyl-cyclopentanol
1-Phenethyl-2-pyrrolidin-1-ylmethyl-cyclopentanol
1-Phenylethynyl-2-pyrrolidin-1-ylmethyl-cyclopentanol
2-Pyrrolidin-1-ylmethyl-1-thiophen-2-yl-cyclopentanol
1-(2,4-Dichloro-phenyl)-2-pyrrolidin-1-ylmethyl-cyclopentanol
1-(3-Phenyl-propyl)-2-pyrrolidin-1-ylmethyl-cyclopentanol
1-(2,3-Dichloro-phenyl)-2-pyrrolidin-1-ylmethyl-cyclopentanol
2-Pyrrolidin-1-ylmethyl-1-p-tolyl-cyclopentanol
1-(4-Methoxy-phenyl)-2-pyrrolidin-1-ylmethyl-cyclopentanol
1-Phenyl-2-pyrrolidin-1-ylmethyl-cycloheptanol
1-(4-Chloro-phenyl)-2-pyrrolidin-1-ylmethyl-cycloheptanol
1-Benzyl-2-pyrrolidin-1-ylmethyl-cycloheptanol
1-(4-Fluoro-3-methyl-phenyl)-2-pyrrolidin-1-ylmethyl-cycloheptanol
2-Pyrrolidin-1-ylmethyl-1-o-tolyl-cycloheptanol
2-Pyrrolidin-1-ylmethyl-1-vinyl-cycloheptanol
1-(4-tert-Butyl-phenyl)-2-pyrrolidin-1-ylmethyl-cycloheptanol
1-Cyclopentyl-2-pyrrolidin-1-ylmethyl-cycloheptanol
2-Pyrrolidin-1-ylmethyl-1-m-tolyl-cycloheptanol
1-Cyclohexyl-2-pyrrolidin-1-ylmethyl-cycloheptanol
1-(4-Fluoro-phenyl)-2-pyrrolidin-1-ylmethyl-cycloheptanol
1-Phenethyl-2-pyrrolidin-1-ylmethyl-cycloheptanol
1-Phenylethynyl-2-pyrrolidin-1-ylmethyl-cycloheptanol
2-Pyrrolidin-1-ylmethyl-1-thiophen-2-yl-cycloheptanol
1-(2,4-Dichloro-phenyl)-2-pyrrolidin-1-ylmethyl-cycloheptanol
1-(3-Phenyl-propyl)-2-pyrrolidin-1-ylmethyl-cycloheptanol
1-(2,3-Dichloro-phenyl)-2-pyrrolidin-1-ylmethyl-cycloheptanol
2-Pyrrolidin-1-ylmethyl-1-p-tolyl-cycloheptanol
1-(4-Methoxy-phenyl)-2-pyrrolidin-1-ylmethyl-cycloheptanol
2-Azepan-1-ylmethyl-1-phenyl-cyclohexanol
2-Azepan-1-ylmethyl-1-benzyl-cyclohexanol
2-Azepan-1-ylmethyl-1-(4-fluoro-3-methyl-phenyl)-cyclohexanol
2-Azepan-1-ylmethyl-1-o-tolyl-cyclohexanol
2-Azepan-1-ylmethyl-1-vinyl-cyclohexanol
2-Azepan-1-ylmethyl-1-(4-tert-butyl-phenyl)-cyclohexanol
2-Azepan-1-ylmethyl-1-cyclopentyl-cyclohexanol
2-Azepan-1-ylmethyl-1-m-tolyl-cyclohexanol
2-Azepan-1-ylmethyl-bicyclohexyl-1-ol
2-Azepan-1-ylmethyl-1-(4-fluoro-phenyl)-cyclohexanol
2-Azepan-1-ylmethyl-1-phenethyl-cyclohexanol
2-Azepan-1-ylmethyl-1-thiophen-2-yl-cyclohexanol
2-Azepan-1-ylmethyl-1-(2,4-dichloro-phenyl)-cyclohexanol
2-Azepan-1-ylmethyl-1-(3-methoxy-phenyl)-cyclohexanol
2-Azepan-1-ylmethyl-1-(3-phenyl-propyl)-cyclohexanol
2-Azepan-1-ylmethyl-1-p-tolyl-cyclohexanol
2-Azepan-1-ylmethyl-1-(4-methoxy-phenyl)-cyclohexanol
2-Azepan-1-ylmethyl-1-phenyl-cyclopentanol
2-Azepan-1-ylmethyl-1-(4-chloro-phenyl)-cyclopentanol
2-Azepan-1-ylmethyl-1-benzyl-cyclopentanol
2-Azepan-1-ylmethyl-1-(4-fluoro-3-methyl-phenyl)-cyclopentanol
2-Azepan-1-ylmethyl-1-o-tolyl-cyclopentanol
2-Azepan-1-ylmethyl-1-vinyl-cyclopentanol
2-Azepan-1-ylmethyl-1-(4-tert-butyl-phenyl)-cyclopentanol
2-Azepan-1-ylmethyl-bicyclopentyl-1-ol
2-Azepan-1-ylmethyl-1-m-tolyl-cyclopentanol 2-Azepan-1-ylmethyl-1-cyclohexyl-cyclopentanol
2-Azepan-1-ylmethyl-1-(4-fluoro-phenyl)-cyclopentanol
2-Azepan-1-ylmethyl-1-phenethyl-cyclopentanol
2-Azepan-1-ylmethyl-1-phenylethynyl-cyclopentanol
2-Azepan-1-ylmethyl-1-thiophen-2-yl-cyclopentanol
2-Azepan-1-ylmethyl-1-(3-methoxy-phenyl)-cyclopentanol
2-Azepan-1-ylmethyl-1-(3-phenyl-propyl)-cyclopentanol
2-Azepan-1-ylmethyl-1-p-tolyl-cyclopentanol
2-Azepan-1-ylmethyl-1-(4-methoxy-phenyl)-cyclopentanol
2-Azepan-1-ylmethyl-1-phenyl-cycloheptanol
2-Azepan-1-ylmethyl-1-benzyl-cycloheptanol
2-Azepan-1-ylmethyl-1-(4-fluoro-3-methyl-phenyl)-cycloheptanol
2-Azepan-1-ylmethyl-1-o-tolyl-cycloheptanol
2-Azepan-1-ylmethyl-1-vinyl-cycloheptanol
2-Azepan-1-ylmethyl-1-(4-tert-butyl-phenyl)-cycloheptanol
2-Azepan-1-ylmethyl-1-cyclopentyl-cycloheptanol
2-Azepan-1-ylmethyl-1-m-tolyl-cycloheptanol
2-Azepan-1-ylmethyl-1-cyclohexyl-cycloheptanol
2-Azepan-1-ylmethyl-1-(4-fluoro-phenyl)-cycloheptanol
2-Azepan-1-ylmethyl-1-phenethyl-cycloheptanol
2-Azepan-1-ylmethyl-1-phenylethynyl-cycloheptanol
2-Azepan-1-ylmethyl-1-thiophen-2-yl-cycloheptanol
2-Azepan-1-ylmethyl-1-(2,4-dichloro-phenyl)-cycloheptanol
2-Azepan-1-ylmethyl-1-(3-methoxy-phenyl)-cycloheptanol
2-Azepan-1-ylmethyl-1-(3-phenyl-propyl)-cycloheptanol
2-Azepan-1-ylmethyl-1-p-tolyl-cycloheptanol
2-Azepan-1-ylmethyl-1-(4-methoxy-phenyl)-cycloheptanol
3-Ethyl-4-methyl-1-phenyl-5-pyrrolidin-1-yl-pent-1-yn-3-ol
3-Benzyl-2-methyl-1-piperidin-1-yl-pentan-3-ol
3-(4-tert-Butyl-phenyl)-2-methyl-1-piperidin-1-yl-pentan-3-ol
3-Cyclopentyl-2-methyl-1-piperidin-1-yl-pentan-3-ol
2-Methyl-1-piperidin-1-yl-3-m-tolyl-pentan-3-ol
3-Cyclohexyl-2-methyl-1-piperidin-1-yl-pentan-3-ol
3-(4-Fluoro-phenyl)-2-methyl-1-piperidin-1-yl-pentan-3-ol
3-Ethyl-2-methyl-5-phenyl-1-piperidin-1-yl-pentan-3-ol
3-Ethyl-4-methyl-1-phenyl-5-piperidin-1-yl-pent-1-yn-3-ol
2-Azepan-1-ylmethyl-1-(3-phenyl-propyl)-cyclopentanol
2-Azepan-1-ylmethyl-1-(2,3-dichloro-phenyl)-cyclopentanol
1-Benzyl-2-piperidin-1-ylmethyl-cyclododecanol
1-(4-tert-Butyl-phenyl)-2-piperidin-1-ylmethyl-cyclododecanol
1-Cyclopentyl-2-piperidin-1-ylmethyl-cyclododecanol
1-Cyclohexyl-2-piperidin-1-ylmethyl-cyclododecanol
1-Phenethyl-2-piperidin-1-ylmethyl-cyclododecanol
1-Phenylethynyl-2-piperidin-1-ylmethyl-cyclododecanol
2-Piperidin-1-ylmethyl-1-thiophen-2-yl-cyclododecanol
1-(3-Phenyl-propyl)-2-piperidin-1-ylmethyl-cyclododecanol
1-(4-Methoxy-phenyl)-2-piperidin-1-ylmethyl-cyclododecanol
2-Azepan-1-ylmethyl-1-benzyl-cyclododecanol
2-Azepan-1-ylmethyl-1-vinyl-cyclododecanol
2-Azepan-1-ylmethyl-1-(4-tert-butyl-phenyl)-cyclododecanol
2-Azepan-1-ylmethyl-1-phenethyl-cyclododecanol
2-Azepan-1-ylmethyl-1-(3-phenyl-propyl)-cyclododecanol
1-Phenyl-2-pyrrolidin-1-ylmethyl-cyclododecanol
1-(4-Chloro-phenyl)-2-pyrrolidin-1-ylmethyl-cyclododecanol
1-(4-tert-Butyl-phenyl)-2-pyrrolidin-1-ylmethyl-cyclododecanol
1-Cyclopentyl-2-pyrrolidin-1-ylmethyl-cyclododecanol
1-(4-Fluoro-3-methyl-phenyl)-2-pyrrolidin-1-ylmethyl-cyclooctanol
2-Pyrrolidin-1-ylmethyl-1-o-tolyl-cyclooctanol
2-Pyrrolidin-1-ylmethyl-1-vinyl-cyclooctanol
2-Piperidin-1-ylmethyl-1-p-tolyl-cyclooctanol
1-Cyclohexylmethyl-2-pyrrolidin-1-ylmethyl-cyclohexanol
1-(4-Chloro-3-trifluormethyl-phenyl)-2-pyrrolidin-1-ylmethyl-cycloheptanol
1-(3-Fluoro-benzyl)-2-pyrrolidin-1-ylmethyl-cycloheptanol
2-Azepan-1-ylmethyl-1-(3-fluoro-phenyl)-cyclohexanol
2-Azepan-1-ylmethyl-1-(3-chloro-phenyl)-cyclohexanol
2-Azepan-1-ylmethyl-1-cyclohexylmethyl-cyclopentanol
2-Azepan-1-ylmethyl-1-(2-chloro-6-fluoro-benzyl)-cyclopentanol
2-Azepan-1-ylmethyl-1-(2,5-dimethyl-benzyl)-cyclopentanol
2-Azepan-1-ylmethyl-1-(4-fluoro-benzyl)-cycloheptanol
2-Azepan-1-ylmethyl-1-(3-methoxy-benzyl)-cycloheptanol
2-Azepan-1-ylmethyl-1-(3-methoxy-benzyl)-cycloheptanol
1-Azepan-1-yl-3-cyclohexylmethyl-2-methyl-pentan-3-ol
1-Azepan-1-yl-3-(5-fluoro-2-methoxy-phenyl)-2-methyl-pentan-3-ol
2-Azepan-1-ylmethyl-1-(3-fluoro-benzyl)-cyclopentanol
1-(4-Fluoro-benzyl)-2-piperidin-1-ylmethyl-cyclododecanol
1-(3-Fluoro-benzyl)-2-piperidin-1-ylmethyl-cyclododecanol
1-(2-Chloro-benzyl)-2-pyrrolidin-1-ylmethyl-cyclododecanol
1-(3-Chloro-phenyl)-2-pyrrolidin-1-ylmethyl-cyclooctanol
2-Azepan-1-ylmethyl-1-(3-phenyl-propyl)-cyclooctanol The pharmaceutical preparations according to the invention may contain the compounds of formula I, preferably corresponding to formula II or III, in the form of the enantiomers thereof or the diastereomers thereof or in the form of a mixture of at least two of the above-stated stereoisomers, including the racemates thereof.

The pharmaceutical preparations according to the invention are particularly suitable for the treatment of pain, as an antiemetic and/or a nootropic (neurotropic), for the treatment of cardiovascular diseases, urinary incontinence, diarrhea, pruritus, dependency on alcohol and/or drugs and/or medicines, and/or inflammation, for the treatment of depression, to increase vigilance and/or libido.

The invention also relates to the use of substituted aminoalcohols corresponding to formula I, preferably corresponding to formula II or III, with the exception of compounds of the formula Ia, to produce pharmaceutical preparations for the treatment of pain as well as the use of substituted aminoalcohols corresponding to formula I, preferably corresponding to formula II or III, for the treatment of emesis, cardiovascular diseases, urinary incontinence, diarrhoea, pruritus, dependency on alcohol and/or drugs and/or medicines, and/or inflammation, for the treatment of depression, to increase drive, vigilance and/or libido.

The pharmaceutical preparations according to the invention may be formulated as liquid, semisolid or solid dosage forms, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, and also be administered as such.

In addition to at least one compound corresponding to formula I, preferably corresponding to formula II or III, the pharmaceutical preparations according to the invention conventionally contain further physiologically acceptable pharmaceutical auxiliary substances, which are preferably selected from the group consisting of matrix materials, fillers, solvents, diluents, surface-active substances, dyes, preservatives, suspending agents, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. Compounds corresponding to formula I, preferably corresponding to formula II or III, in a depot in dissolved form or in a dressing, optionally with the addition of skin penetration promoters, are suitable percutaneous administration preparations.

Production of the pharmaceutical preparations according to the invention proceeds with the assistance of conventional means, devices, methods and processes known to the person skilled in the art, such as are described for example in "Remington's Pharmaceutical Sciences", ed. A. R. Gennaro, 17th ed., Mack Publishing Company, Easton, Pa. (1985), in particular in part 8, chapters 76 to 93. The corresponding literature description is hereby introduced as a reference and is deemed to be part of the disclosure.

The quantity of the respective compound corresponding to formula I, preferably corresponding to formula II or III, to be administered to the patient may vary and is for example dependent on the weight or age of the patient and on the mode of administration, the indication and the severity of the complaint. Conventionally, at least one compound corresponding to formula I, preferably corresponding to formula II or III, is administered in a quantity of 0.005 to 500 mg/kg, preferably of 0.05 to 5 mg/kg, of patient body weight.

The invention further provides 2-(aminomethyl)-cycloalkan-1-ol compounds corresponding to formula III,

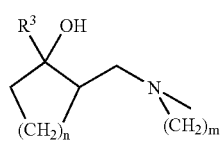

III in which
n denotes an integer from 2 to 9 and m denotes an integer from 4 to 6 in the following combinations,

| n | m |
|---|---|
| 2 | 4 |
| 2 | 6 |
| 3 | 6 |
| 4 | 4 |
| 4 | 6 |
| 5 | 4 |
| 5 | 5 |
| 5 | 6 |

-continued

| n | m |
|---|---|
| 9 | 4 |
| 9 | 5 |
| 9 | 6 | wherein optionally one or more $CH_2$ groups of the $(CH_2)_m$ chain may be replaced by oxygen, $R^3$ denotes a linear or branched, saturated or unsaturated aliphatic residue, a saturated or unsaturated cycloaliphatic residue, an aryl residue or a heteroaryl residue, wherein the respective ring system may be optionally mono- or polysubstituted and/or attached via a linear or branched, saturated or unsaturated aliphatic bridge and/or the aryl or heteroaryl residue may be part of a polycyclic system in the form of the pure diastereomers thereof, the pure enantiomers thereof and mixtures thereof—including the racemates thereof—and in the form of corresponding bases, salts and solvates.

Compounds corresponding to formula III are preferred, in which $R^3$ denotes a linear or branched, saturated or unsaturated aliphatic $C_{1-6}$ residue, a saturated or unsaturated cycloaliphatic $C_{3-7}$ residue, a phenyl residue or a five- or six-membered heteroaryl residue, wherein the respective ring system may optionally be mono- or polysubstituted and/or attached via a linear or branched, saturated or unsaturated aliphatic $C_{1-5}$ bridge, and the other symbols have the above-stated meanings.

Compounds corresponding to formula III are additionally preferred, in which $R^3$ denotes a linear or branched, saturated or unsaturated aliphatic $C_{1-3}$ residue, a saturated or unsaturated cycloaliphatic $C_{5-6}$ residue, a phenyl residue or a five- or six-membered heteroaryl residue, wherein the respective ring system may optionally be mono- or polysubstituted with halogen, an alkyl group, an alkoxy group and/or a trihalogenated alkyl group and/or may be attached via a linear or branched, saturated or unsaturated aliphatic $C_{1-3}$ bridge and the other symbols have the above-stated meanings.

Compounds corresponding to formula III are additionally preferred, in which $R^3$ denotes a vinyl residue, a cyclopentyl residue, a cyclohexyl residue, a thiophenyl residue or a phenyl residue, wherein the cyclohexyl residue may optionally be attached via a methylene bridge or the phenyl residue may optionally be mono- or polysubstituted with fluorine, chlorine, a methyl group, an isopropyl group, a methoxy group and/or a trifluoromethyl group and/or may optionally be attached via a linear saturated aliphatic $C_{1-3}$ bridge or an ethynyl bridge and the other symbols have the above-stated meanings.

The invention also provides a process for the production of certain compounds according to the invention in which A) a ketone of the formula (1), in which n is a whole number from 2 to 9,

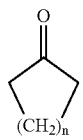

(1)

is reacted with paraformaldehyde and a cyclic amine of the formula (2), in which m is whole number from 4 to 6,

(2)

according to a Mannich reaction in a suitable solvent, preferably in ethanol with the addition of hydrochloric acid or in acetic acid, with heating, then the reaction mixture is worked up and the product of formula (3) is isolated and optionally purified; or

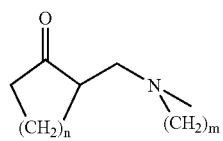

(3)

B) a compound of the formula (3) is reacted with a Grignard compound or an organolithium compound of the formulae $R^3MgCl$, $R^3MgBr$, $R^3MgI$, $MgR^3_2$ or $LiR^3$, in which $R^3$ denotes a linear or branched, saturated or unsaturated aliphatic $C_{1-3}$ residue, a saturated or unsaturated cycloaliphatic $C_{5-6}$ residue, a phenyl residue or a five- or six-membered heteroaryl residue, wherein the respective ring system may optionally be mono- or polysubstituted with halogen, an alkyl group, an alkoxy group and/or a trihalogenated alkyl group and/or may be attached via a linear or branched, saturated or unsaturated aliphatic $C_{1-3}$ bridge, in a suitable solvent, preferably diethyl ether or tetrahydrofuran, then the reaction mixture is worked up and the compound corresponding to formula I is isolated and optionally purified.

The starting compounds used are commercially available or may be obtained using conventional methods known to the person skilled in the art. The reactions are known to persons skilled in the art from the literature. The solvents and reaction conditions used for the respective process step correspond to the solvents and reaction conditions conventional for these types of reactions.

The free bases of the respective compounds according to the invention corresponding to formula III may be converted into the corresponding physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid. The salts formed comprise, inter alia, hydrochlorides, hydrobromides, phosphates, carbonates, hydrogencarbonates, formates, acetates, oxalates, succinates, tartrates, fumarates, citrates and glutamates.

The free bases of the respective compounds according to the invention corresponding to formula III may be converted into the corresponding hydrochlorides by combining the compounds according to the invention corresponding to formula I as free bases dissolved in a suitable organic solvent, such as for example butan-2-one (methyl ethyl ketone), with trimethylsilyl chloride (TMSCl). They may also be converted into the hydrobromides in a corresponding manner.

The hydrates may be formed by crystallisation from an aqueous solution.

If the compounds according to the invention corresponding to formula III are obtained by the production process according to the invention in the form of the racemates thereof or other mixtures of their various enantiomers and/or diastereomers, these may be separated and optionally isolated by conventional processes known to the person skilled in the art. Examples are chromatographic separation processes, in particular liquid chromatography processes at standard pressure or at elevated pressure, preferably MPLC and HPLC processes, and fractional crystallisation processes. Individual enantiomers, e.g. diastereomeric salts formed by means of HPLC on a chiral phase or by means of crystallisation with chiral acids, such as (+)-tartaric acid, (−)-tartaric acid or (+)-10-camphorsulfonic acid, may here in particular be separated from one another.

The compounds corresponding to formula III according to the invention are toxicologically safe and are therefore suitable as pharmaceutical active ingredients in pharmaceutical preparations.

EXAMPLES

Preparation

Mannich Reaction

One equivalent of the amine hydrochloride, 1-1.5 equivalents of the ketone and 1-1.2 equivalents of paraformaldehyde in 8-10 equivalents of acetic acid were heated with stirring for 15-20 minutes to 95-98° C. Then the acetic acid was removed by vacuum-distillation under mild conditions and the reaction mixture combined with acetone or successively with acetone and diisopropyl ether. The Mannich compound precipitated out in crystalline form as the hydrochloride.

It was possible, in some cases, advantageously to perform the Mannich reaction in ethanol, combined with a few drops of concentrated hydrochloric acid, with refluxing for several hours (at most 5 to 7 hours).

Further purification of the Mannich compound was effected, where necessary, by silica gel chromatography with ethyl acetate as eluent.

Grignard Reaction

The Mannich compound dissolved in THF (400 µl, 0.5 M) was initially introduced into a heat-treated reaction vessel cooled to −10° C. under inert gas. 2 equivalents of the prepared Grignard or organolithium reagent in THF or diethyl ether (800 µl, 0.5 M) were then added with stirring. The reaction mixture was stirred at room temperature. After three hours it was recooled to −10° C. and hydrolysed with ammonium chloride solution.

The reaction mixture was extracted twice with ethyl acetate and vacuum-evaporated at 40° C.

To characterise the product, an ESI-MS spectrograph was recorded.

Biological Data:

Investigations Relating to Noradrenaline Reuptake Inhibition (NA Uptake Inhibition)

The compounds according to the invention are NA uptake inhibitors. In order to be able to carry out these in vitro studies, synaptosomes were freshly isolated from rat brain regions. A so-called "$P_2$" fraction was used, which was prepared according to the instructions given by Gray and Whittaker (E. G. Gray and V. P. Whittaker (1962) J. Anat. 76, 79-88). For NA uptake, these vesicular particles were isolated from the hypothalamus of male rat brains.

The following characteristics were determined for the NA transporter:

NA uptake: Km=0.32±0.11 µM (In each case N=4, i.e. means±SEM from 4 independent series of tests, which were performed as parallel tests in triplicate).

A detailed description of the method may be found in the literature (M. Ch. Frink, H.-H. Hennies, W. Englberger, M. Haurand and B. Wilffert (1996) Arzneim.-Forsch./Drug Res. 46 (III), 11, 1029-1036). The NA uptake inhibition of selected compounds was determined. The values were determined at a test concentration of $10^{-5}$ M.

| Example | NA Uptake (% inhibition) |
| --- | --- |
| 1-(2,3-Dichloro-phenyl)-2-pyrrolidin-1-ylmethyl-cyclohexanol | 60 |
| 2-Pyrrolidin-1-ylmethyl-1-p-tolyl-cyclohexanol | 59 |
| 1-(4-Chloro-phenyl)-2-pyrrolidin-1-ylmethyl-cyclopentanol | 68 |
| 1-(4-Fluoro-3-methyl-phenyl)-2-pyrrolidin-1-ylmethyl-cyclopentanol | 59 |
| 2-Pyrrolidin-1-ylmethyl-1-m-tolyl-cyclopentanol | 52 |
| 1-Phenethyl-2-pyrrolidin-1-ylmethyl-cyclopentanol | 59 |
| 1-Phenylethynyl-2-pyrrolidin-1-ylmethyl-cyclopentanol | 92 |
| 1-(3-Phenyl-propyl)-2-pyrrolidin-1-ylmethyl-cyclopentanol | 65 |
| 1-(2,3-Dichloro-phenyl)-2-pyrrolidin-1-ylmethyl-cyclopentanol | 53 |
| 2-Pyrrolidin-1-ylmethyl-1-p-tolyl-cyclopentanol | 78 |
| 1-Phenyl-2-pyrrolidin-1-ylmethyl-cycloheptanol | 56 |
| 1-(4-Chloro-phenyl)-2-pyrrolidin-1-ylmethyl-cycloheptanol | 75 |
| 1-(4-Fluoro-3-methyl-phenyl)-2-pyrrolidin-1-ylmethyl-cycloheptanol | 83 |
| 2-Pyrrolidin-1-ylmethyl-1-m-tolyl-cycloheptanol | 67 |
| 1-(4-Fluoro-phenyl)-2-pyrrolidin-1-ylmethyl-cycloheptanol | 57 |
| 1-Phenethyl-2-pyrrolidin-1-ylmethyl-cycloheptanol | 82 |
| 1-Phenylethynyl-2-pyrrolidin-1-ylmethyl-cycloheptanol | 66 |
| 1-(2,4-Dichloro-phenyl)-2-pyrrolidin-1-ylmethyl-cycloheptanol | 55 |
| 1-(3-Phenyl-propyl)-2-pyrrolidin-1-ylmethyl-cycloheptanol | 63 |
| 1-(2,3-Dichloro-phenyl)-2-pyrrolidin-1-ylmethyl-cycloheptanol | 63 |
| 2-Pyrrolidin-1-ylmethyl-1-p-tolyl-cycloheptanol | 76 |
| 1-(4-Methoxy-phenyl)-2-pyrrolidin-1-ylmethyl-cycloheptanol | 69 |
| 2-Azepan-1-ylmethyl-1-(4-fluoro-3-methyl-phenyl)-cyclohexanol | 54 |
| 2-Azepan-1-ylmethyl-1-(4-fluoro-phenyl)-cyclohexanol | 52 |
| 2-Azepan-1-ylmethyl-1-phenethyl-cyclohexanol | 70 |
| 2-Azepan-1-ylmethyl-1-(3-phenyl-propyl)-cyclohexanol | 77 |
| 2-Azepan-1-ylmethyl-1-p-tolyl-cyclohexanol | 64 |
| 2-Azepan-1-ylmethyl-1-(4-methoxy-phenyl)-cyclohexanol | 58 |
| 2-Azepan-1-ylmethyl-1-(4-chloro-phenyl)-cyclopentanol | 80 |
| 2-Azepan-1-ylmethyl-1-(4-fluoro-3-methyl-phenyl)-cyclopentanol | 73 |
| 2-Azepan-1-ylmethyl-1-m-tolyl-cyclopentanol | 59 |
| 2-Azepan-1-ylmethyl-1-phenethyl-cyclopentanol | 92 |
| 2-Azepan-1-ylmethyl-1-phenylethynyl-cyclopentanol | 99 |
| 2-Azepan-1-ylmethyl-1-thiophen-2-yl-cyclopentanol | 51 |
| 2-Azepan-1-ylmethyl-1-(3-phenyl-propyl)-cyclopentanol | 59 |
| 2-Azepan-1-ylmethyl-1-p-tolyl-cyclopentanol | 70 |
| 2-Azepan-1-ylmethyl-1-(4-methoxy-phenyl)-cyclopentanol | 58 |
| 2-Azepan-1-ylmethyl-1-phenyl-cycloheptanol | 52 |
| 2-Azepan-1-ylmethyl-1-benzyl-cycloheptanol | 55 |
| 2-Azepan-1-ylmethyl-1-(4-fluoro-3-methyl-phenyl)-cycloheptanol | 63 |
| 2-Azepan-1-ylmethyl-1-phenethyl-cycloheptanol | 87 |
| 2-Azepan-1-ylmethyl-1-p-tolyl-cycloheptanol | 58 |
| 2-Azepan-1-ylmethyl-1-(4-methoxy-phenyl)-cycloheptanol | 58 |
| 3-Ethyl-4-methyl-1-phenyl-5-pyrrolidin-1-yl-pent-1-yn-3-ol | 76 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A pharmaceutical preparation comprising at least one substituted aminoalcohol corresponding to formula I

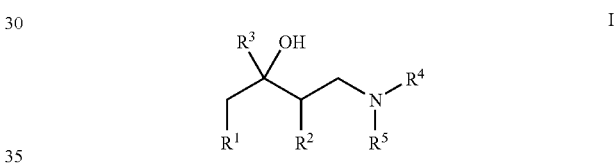

wherein
R$^1$ and R$^2$ together form a (CH$_2$)$_n$ chain, wherein n denotes an integer from 2 to 9,
R$^3$ denotes a saturated or unsaturated cycloaliphatic group which is unsubstituted or mono- or polysubstituted with halogen, alkyl, alkoxy or trihalogenated alkyl, an aryl group which is mono- or polysubstituted with halogen, alkyl or trihalogenated alkyl, or a heteroaryl group which is unsubstituted or mono- or polysubstituted with halogen, alkyl, alkoxy or trihalogenated alkyl; or a saturated or unsaturated cycloaliphatic, aryl or heteroaryl group which is attached via a linear or branched, saturated or unsaturated aliphatic bridge and is unsubstituted or mono- or polysubstituted with halogen, alkyl, alkoxy or trihalogenated alkyl; wherein the aryl or heteroaryl group may be monocyclic or polycyclic, and
R$^4$ and R$^5$ together form a (CH$_2$)$_m$ chain, wherein m denotes 6 and optionally one or more CH$_2$ groups may be replaced by oxygen,
or a pharmaceutically acceptable salt or solvate thereof; and optionally one or more physiologically acceptable auxiliary substances.

2. A preparation according to claim 1, wherein in said substituted aminoalcohol:
R$^1$ and R$^2$ together form a (CH$_2$)$_n$ chain, wherein n denotes an integer from 2-9;
R$^3$ denotes a saturated or unsaturated cycloaliphatic C$_{3-7}$ group which is unsubstituted or mono- or polysubstituted with halogen, alkyl, alkoxy or trihalogenated alkyl, a phenyl group which is mono- or polysubstituted with halogen, alkyl or trihalogenated alkyl, or a five- or six-membered heteroaryl group which is unsubstituted or mono- or polysubstituted with halogen, alkyl, alkoxy or trihalogenated alkyl; or a saturated or unsaturated cycloaliphatic $C_{3-7}$ group, phenyl group or five- or six-membered heteroaryl group which is attached via a linear or branched, saturated or unsaturated aliphatic $C_{1-5}$ bridge and is unsubstituted or mono- or polysubstituted with halogen, alkyl, alkoxy or trihalogenated alkyl; and $R^4$ and $R^5$ together form a $(CH_2)_m$ chain, wherein m denotes 6 and optionally one or more $CH_2$ groups may be replaced by oxygen.

3. A preparation according to claim 1, wherein in said substituted aminoalcohol:

$R^1$ and $R^2$ together form a $(CH_2)_n$ chain, wherein n denotes an integer from 2-9;

$R^3$ denotes a saturated or unsaturated cycloaliphatic $C_{5-6}$ group which is unsubstituted or mono- or polysubstituted with halogen, alkyl, alkoxy or trihalogenated alkyl, a phenyl group which is mono- or polysubstituted with halogen, alkyl or trihalogenated alkyl, or a five- or six-membered heteroaryl group which is unsubstituted or mono- or polysubstituted with halogen, alkyl, alkoxy or trihalogenated alkyl; or a saturated or unsaturated cycloaliphatic $C_{5-6}$ group, phenyl group or five- or six-membered heteroaryl group which is attached via a linear or branched, saturated or unsaturated aliphatic $C_{1-3}$ bridge and is unsubstituted or mono- or polysubstituted with halogen, alkyl, alkoxy or trihalogenated alkyl; and $R^4$ and $R^5$ together form a $(CH_2)_m$ chain, wherein m denotes 6 and optionally one or more $CH_2$ groups may be replaced by oxygen.

4. A preparation according to claim 1, wherein in said substituted aminoalcohol:

$R^1$ and $R^2$ together form a $(CH_2)_n$ chain, wherein n denotes 2, 3, 4, 5 or 9;

$R^3$ denotes a cyclopentyl group, a cyclohexyl group, a thiophenyl group, or a phenyl group which is mono- or polysubstituted with halogen, alkyl or trihalogenated alkyl, or a cyclohexyl group which is attached via a methylene bridge, or a phenyl group which is attached via a linear saturated aliphatic $C_{1-3}$ bridge or an ethynyl bridge and is unsubstituted or mono- or polysubstituted by halogen, alkyl, alkoxy or trihalogenated alkyl; and $R^4$ and $R^5$ together form a $(CH_2)_m$ chain, wherein m denotes 6.

5. A preparation according to claim 1, wherein said at least one substituted aminoalcohol corresponds to formula III

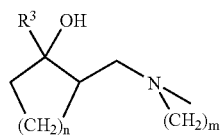

III wherein n denotes an integer from 2-9, and m denotes 6.

6. A preparation according to claim 5, wherein $R^3$ denotes a saturated or unsaturated cycloaliphatic $C_{3-7}$ group which is unsubstituted or mono- or polysubstituted by halogen, alkyl, alkoxy or trihalogenated alkyl, a phenyl group which is mono- or polysubstituted with halogen, alkyl or trihalogenated alkyl, or a five- or six-membered heteroaryl group which is unsubstituted or mono- or polysubstituted with halogen, alkyl, alkoxy or trihalogenated alkyl; or a saturated or unsaturated cycloaliphatic $C_{3-7}$ group, phenyl group or five- or six-membered heteroaryl group which is attached via a linear or branched, saturated or unsaturated aliphatic $C_{1-5}$ bridge and is unsubstituted or mono- or polysubstituted with halogen, alkyl, alkoxy or trihalogenated alkyl.

7. A preparation according to claim 5, wherein $R^3$ denotes a saturated or unsaturated cycloaliphatic $C_{5-6}$ group which is unsubstituted or mono- or polysubstituted with halogen, alkyl, alkoxy or trihalogenated alkyl, a phenyl group which is mono- or polysubstituted with halogen, alkyl or trihalogenated alkyl, or a five- or six-membered heteroaryl group which is unsubstituted or mono- or polysubstituted with halogen, alkyl, alkoxy or trihalogenated alkyl; or a saturated or unsaturated cycloaliphatic $C_{5-6}$ group, phenyl group or five- or six-membered heteroaryl group which is attached via a linear or branched, saturated or unsaturated aliphatic $C_{1-3}$ bridge and is unsubstituted or mono- or polysubstituted by halogen, alkyl, alkoxy or trihalogenated alkyl.

8. A preparation according to claim 5, wherein $R^3$ denotes a cyclopentyl group, a cyclohexyl group, a thiophenyl group, or a phenyl group which is mono- or polysubstituted with halogen, alkyl or trihalogenated alkyl, or a cyclohexyl group which is attached via a methylene bridge, or a phenyl group which is attached via a linear saturated aliphatic $C_{1-3}$ bridge or an ethynyl bridge and is unsubstituted or mono- or polysubstituted with halogen, alkyl, alkoxy or trihalogenated alkyl.

9. A pharmaceutical preparation comprising at least one substituted aminoalcohol selected from the group consisting of:
1-(2,3-dichlorophenyl)-2-pyrrolidin-1-ylmethyl-cyclohexanol,
2-pyrrolidin-1-ylmethyl-1-p-tolyl-cyclohexanol,
1-(4-chlorophenyl)-2-pyrrolidin-1-ylmethyl-cyclopentanol,
1-benzyl-2-pyrrolidin-1-ylmethyl-cyclopentanol,
1-(4-fluoro-3-methylphenyl)-2-pyrrolidin-1-ylmethyl-cyclopentanol,
2-pyrrolidin-1-ylmethyl-1-o-tolyl-cyclopentanol,
2-pyrrolidlin-1-ylmethyl-1-vinyl-cyclopentanol,
1-(4-tert-butyl-phenyl)-2-pyrrolidin-1-ylmethyl-cyclopentanol,
2-pyrrolidin-1-ylmethyl-bicyclopentyl-1-ol,
2-pyrrolidin-1-ylmethyl-1-m-tolyl-cyclopentanol,
1-cyclohexyl-2-pyrrolidin-1-ylmethyl-cyclopentanol,
1-(4-fluorophenyl)-2-pyrrolidin-1-ylmethyl-cyclopentanol,
1-phenethyl-2-pyrrolidin-1-ylmethyl-cyclopentanol,
1-phenylethynyl-2-pyrrolidin-1-ylmethyl-cyclopentanol,
2-pyrrolidin-1-ylmethyl-1-thiophen-2-yl-cyclopentanol,
1-(2,4-dichlorophenyl)-2-pyrrolidin-1-ylmethyl-cyclopentanol,
1-(3-phenylpropyl)-2-pyrrolidin-1-ylmethyl-cyclopentanol,
1-(2,3-dichlorophenyl)-2-pyrrolidin-1-ylmethyl-cyclopentanol,
2-pyrrolidin-1-ylmethyl-1-p-tolyl-cyclopentanol,
1-(4-chlorophenyl)-2-pyrrolidin-1-ylmethyl-cycloheptanol,
1-benzyl-2-pyrrolidin-1-ylmethyl-cycloheptanol,
1-(4-fluoro-3-methyl-phenyl)-2-pyrrolidin-1-ylmethyl-cycloheptanol,
2-pyrrolidin-1-ylmethyl-1-o-tolyl-cycloheptanol,
2-pyrrolidin-1-ylmethyl-1-vinyl-cycloheptanol,
1-(4-tert-butylphenyl)-2-pyrrolidin-1-ylmethyl-cycloheptanol,
1-cyclopentyl-2-pyrrolidin-1-ylmethyl-cycloheptanol,
2-pyrrolidin-1-ylmethyl-1-m-tolyl-cycloheptanol,
1-cyclohexyl-2-pyrrolidin-1-ylmethyl-cycloheptanol, 1-(4-fluorophenyl)-2-pyrrolidin-1-ylmethyl-cycloheptanol,
1-phenethyl-2-pyrrolidin-1-ylmethyl-cycloheptanol,
1-phenylethynyl-2-pyrrolidin-1-ylmethyl-cycloheptanol,
2-pyrrolidin-1-ylmethyl-1-thiophen-2-yl-cycloheptanol,
1-(2,4-dichlorophenyl)-2-pyrrolidin-1-ylmethyl-cycloheptanol,
1-(3-phenylpropyl)-2-pyrrolidin-1-ylmethyl-cycloheptanol,
1-(2,3-dichlorophenyl)-2-pyrrolidin-1-ylmethyl-cycloheptanol,
2-pyrrolidin-1-ylmethyl-1-p-tolyl-cycloheptanol,
2-azepan-1-ylmethyl-1-benzyl-cyclohexanol,
2-azepan-1-ylmethyl-1-(4-fluoro-3-methylphenyl)-cyclohexanol,
2-azepan-1-ylmethyl-1-o-tolyl-cyclohexanol,
2-azepan-1-ylmethyl-1-vinyl-cyclohexanol,
2-azepan-1-ylmethyl-1-(4-tert-butylphenyl)-cyclohexanol,
2-azepan-1-ylmethyl-1-cyclopentyl-cyclohexanol,
2-azepan-1-ylmethyl-1-m-tolyl-cyclohexanol,
2-azepan-1-ylmethyl-bicyclohexyl-1-ol,
2-azepan-1-ylmethyl-1-(4-fluorophenyl)-cyclohexanol,
2-azepan-1-ylmethyl-1-phenethyl-cyclohexanol,
2-azepan-1-ylmethyl-1-thiophen-2-yl-cyclohexanol,
2-azepan-1-ylmethyl-1-(2,4-dichlorophenyl)-cyclohexanol,
2-azepan-1-ylmethyl-1-(3-phenylpropyl)-cyclohexanol,
2-azepan-1-ylmethyl-1-p-tolyl-cyclohexanol,
2-azepan-1-ylmethyl-1-(4-chlorophenyl)-cyclopentanol,
2-azepan-1-ylmethyl-1-benzyl-cyclopentanol,
2-azepan-1-ylmethyl-1-(4-fluoro-3-methylphenyl)-cyclopentanol,
2-azepan-1-ylmethyl-1-o-tolyl-cyclopentanol,
2-azepan-1-ylmethyl-1-vinyl-cyclopentanol,
2-azepan-1-ylmethyl-1-(4-tert-butylphenyl)-cyclopentanol,
2-azepan-1-ylmethyl-bicyclopentyl-1-ol,
2-azepan-1-ylmethyl-1-m-tolyl-cyclopentanol,
2-azepan-1-ylmethyl-1-cyclohexyl-cyclopentanol,
2-azepan-1-ylmethyl-1-(4-fluorophenyl)-cyclopentanol,
2-azepan-1-ylmethyl-1-phenethyl-cyclopentanol,
2-azepan-1-ylmethyl-1-phenylethynyl-cyclopentanol,
2-azepan-1-ylmethyl-1-thiophen-2-yl-cyclopentanol,
2-azepan-1-ylmethyl-1-(3-phenylpropyl)-cyclopentanol,
2-azepan-1-ylmethyl-1-p-tolyl-cyclopentanol,
2-azepan-1-ylmethyl-1-benzyl-cycloheptanol,
2-azepan-1-ylmethyl-1-(4-fluoro-3-methylphenyl)-cycloheptanol,
2-azepan-1-ylmethyl-1-o-tolyl-cycloheptanol,
2-azepan-1-ylmethyl-1-vinyl-cycloheptanol,
2-azepan-1-ylmethyl-1-(4-tert-butylphenyl)-cycloheptanol,
2-azepan-1-ylmethyl-1-cyclopentyl-cycloheptanol,
2-azepan-1-ylmethyl-1-m-tolyl-cycloheptanol,
2-azepan-1-ylmethyl-1-cyclohexyl-cycloheptanol,
2-azepan-1-ylmethyl-1-(4-fluorophenyl)-cycloheptanol,
2-azepan-1-ylmethyl-1-phenethyl-cycloheptanol,
2-azepan-1-ylmethyl-1-phenylethynyl-cycloheptanol,
2-azepan-1-ylmethyl-1-thiophen-2-yl-cycloheptanol,
2-azepan-1-ylmethyl-1-(2,4-dichlorophenyl)-cycloheptanol,
2-azepan-1-ylmethyl-1-(3-phenylpropyl)-cycloheptanol,
2-azepan-1-ylmethyl-1-p-tolyl-cycloheptanol,
2-azepan-1-ylmethyl-1-(3-phenylpropyl)-cyclopentanol,
2-azepan-1-ylmethyl-1-(2,3-dichlorophenyl)-cyclopentanol,
1-benzyl-2-piperidin-1-ylmethyl-cyclododecanol,
1-(4-tert-butylphenyl)-2-piperidin-1-ylmethyl-cyclododecanol,
1-cyclopentyl-2-piperidin-1-ylmethyl-cyclododecanol,
1-cyclohexyl-2-piperidin-1-ylmethyl-cyclododecanol,
1-phenethyl-2-piperidin-1-ylmethyl-cyclododecanol,
1-phenylethynyl-2-piperidin-1-ylmethyl-cyclododecanol,
2-piperidin-1-ylmethyl-1-thiophen-2-yl-cyclododecanol,
1-(3-phenylpropyl)-2-piperidin-1-ylmethyl-cyclododecanol,
2-azepan-1-ylmethyl-1-benzyl-cyclododecanol,
2-azepan-1-ylmethyl-1-vinyl-cyclododecanol,
2-azepan-1-ylmethyl-1-(4-tert-butylphenyl)-cyclododecanol,
2-azepan-1-ylmethyl-1-phenethyl-cyclododecanol,
2-azepan-1-ylmethyl-1-(3-phenyl-propyl)-cyclododecanol,
1-(4-chlorophenyl)-2-pyrrolidin-1-ylmethyl-cyclododecanol,
1-(4-tert-butylphenyl)-2-pyrrolidin-1-ylmethyl-cyclododecanol,
1-cyclopentyl-2-pyrrolidin-1-ylmethyl-cyclododecanol,
1-(4-fluoro-3-methylphenyl)-2-pyrrolidin-1-ylmethyl-cyclooctanol,
2-pyrrolidin-1-ylmethyl-1-o-tolyl-cyclooctanol,
2-pyrrolidin-1-ylmethyl-1-vinyl-cyclooctanol,
2-piperidin-1-ylmethyl-1-p-tolyl-cyclooctanol,
1-cyclohexylmethyl-2-pyrrolidin-1-ylmethyl-cyclohexanol,
1-(4-chloro-3-trifluormethylphenyl)-2-pyrrolidin-1-ylmethyl-cycloheptanol,
1-(3-fluorobenzyl)-2-pyrrolidin-1-ylmethyl-cycloheptanol,
2-azepan-1-ylmethyl-1-(3-fluorophenyl)-cyclohexanol,
2-azepan-1-ylmethyl-1-(3-chlorophenyl)-cyclohexanol,
2-azepan-1-ylmethyl-1-cyclohexylmethyl-cyclopentanol,
2-azepan-1-ylmethyl-1-(2-chloro-6-fluorobenzyl)-cyclopentanol,
2-azepan-1-ylmethyl-1-(2,5-dimethylbenzyl)-cyclopentanol,
2-azepan-1-ylmethyl-1-(4-fluorobenzyl)-cycloheptanol,
2-azepan-1-ylmethyl-1-(3-methoxybenzyl)-cycloheptanol,
2-azepan-1-ylmethyl-1-(3-methoxybenzyl)-cycloheptanol,
2-azepan-1-ylmethyl-1-(3-fluorobenzyl)-cyclopentanol,
1-(4-fluorobenzyl)-2-piperidin-1-ylmethyl-cyclododecanol,
1-(3-fluorobenzyl)-2-piperidin-1-ylmethyl-cyclododecanol,
1-(2-chlorobenzyl)-2-pyrrolidin-1-ylmethyl-cyclododecanol,
1-(3-chlorophenyl)-2-pyrrolidin-1-ylmethyl-cyclooctanol,
2-azepan-1-ylmethyl-1-(3-phenylpropyl)-cyclooctanol,
and pharmaceutically acceptable salts or solvates thereof.

10. A method of treating pain, said method comprising administering to a patient in need thereof an effective pain alleviating amount of a preparation according to claim 1.

11. A 2-(aminomethyl)-cycloalkane-1-ol compound corresponding to formula III

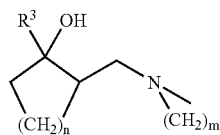

wherein
n denotes an integer from 2-9, and m denotes an integer from 4-6 in the following combinations:

| N | M |
|---|---|
| 2 | 4 |
| 2 | 6 |
| 3 | 6 |
| 4 | 4 |
| 4 | 5 |
| 4 | 6 |
| 5 | 4 |
| 5 | 5 |
| 5 | 6 |
| 9 | 4 |
| 9 | 5 |
| 9 | 6 | wherein optionally one or more $CH_2$ groups of the $(CH_2)_m$ chain may be replaced by oxygen, $R^3$ denotes a saturated or unsaturated cycloaliphatic group which is unsubstituted or mono- or polysubstituted by halogen, alkyl, alkoxy or trihalogenated alkyl; an aryl group which is mono- or polysubstituted by halogen, alkyl or trihalogenated alkyl; or a heteroaryl group which is unsubstituted or mono- or polysubstituted by halogen, alkyl, alkoxy or trihalogenated alkyl; or a saturated or unsaturated cycloaliphatic, aryl or heteroaryl group which is attached via a linear or branched, saturated or unsaturated aliphatic bridge and is unsubstituted or mono- or polysubstituted by halogen, alkyl, alkoxy or trihalogenated alkyl; wherein the aryl or heteroaryl group may be monocyclic or polycyclic, or a pharmaceutically acceptable salt or solvate thereof.

12. A compound according to claim 11, wherein said compound is present in the form of a diastereomer thereof or an enantiomer thereof.

13. A compound according to claim 11, wherein said compound is present in the form of a mixture of diasteromers or a mixture of enantiomers.

14. A compound according to claim 13, wherein said mixture is a racemic mixture.

15. A compound according to claim 11, wherein $R^3$ denotes a saturated or unsaturated cycloaliphatic $C_{3-7}$ group which is unsubstituted or mono- or polysubstituted by halogen, alkyl, alkoxy or trihalogenated alkyl; a phenyl group which is mono- or polysubstituted by halogen, alkyl or trihalogenated alkyl; or a five- or six-membered heteroaryl group which is unsubstituted or mono- or polysubstituted with halogen, alkyl, alkoxy or trihalogenated alkyl; or a saturated or unsaturated cycloaliphatic $C_{3-7}$ group, phenyl group or five- or six-membered heteroaryl group which is attached via a linear or branched, saturated or unsaturated aliphatic $C_{1-5}$ bridge and which is unsubstituted or mono- or polysubstituted with halogen, alkyl, alkoxy, or trihaloalkyl.

16. A compound according to claim 11, wherein $R^3$ denotes a saturated or unsaturated cycloaliphatic $C_{5-6}$ group, a phenyl group, or a five- or six-membered heteroaryl group, wherein said cycloaliphatic, phenyl or heteroaryl group is mono- or polysubstituted with halogen, alkyl, or trihalogenated alkyl; or a saturated or unsaturated cycloaliphatic $C_{5-6}$ group, a phenyl group or a five- or six-membered heteroaryl group which is attached via a linear or branched, saturated or unsaturated aliphatic $C_{1-3}$ bridge and which is unsubstituted or mono- or polysubstituted with halogen, alkyl, alkoxy, or trihaloalkyl.

17. A compound according to claim 11, wherein $R^3$ denotes a cyclopentyl group, a cyclohexyl group, a thiophenyl group, or a phenyl group mono- or polysubstituted with fluorine, chlorine, methyl, isopropyl, methoxy or trifluoromethyl, or a cyclohexyl group which is attached via a methylene bridge; or a phenyl group which is attached via a linear saturated aliphatic $C_{1-3}$ bridge or an ethynyl bridge and which is unsubstituted or mono- or polysubstituted with fluorine, chlorine, methyl, isopropyl, methoxy or trifluoromethyl.

18. A process for producing a compound according to claim 11, said process comprising:

A) reacting a ketone of formula (1), in which n has the meaning stated in claim 11,

with paraformaldehyde and a cyclic amine of the formula (2), in which m has the meaning stated in claim 11,

according to a Mannich reaction in a suitable solvent with heating, and isolating a product corresponding to formula (3)

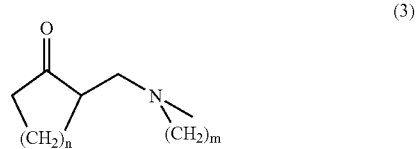

or

B) reacting a compound of formula (3) with a Grignard compound or an organolithium compound corresponding to one of the formulas $R^3MgCl$, $R^3MgBr$, $R^3MgI$, $MgR^3{}_2$ or $LiR^3$, in which $R^3$ has the meaning stated in claim 11, in a suitable solvent, and isolating a compound corresponding to formula III.

19. A process according to claim 18, wherein the reacting in A) is carried out in ethanol with the addition of hydrochloric acid or in acetic acid.

20. A process according to claim 18, wherein the reacting in B) is carried out in diethyl ether or tetrahydrofuran.

* * * * *